United States Patent

Urtti et al.

[11] Patent Number: 5,817,332
[45] Date of Patent: Oct. 6, 1998

[54] TRANSDERMAL DRUG DELIVERY SYSTEM

[76] Inventors: Arto O. Urtti, Isokaari 29, FIN-70420 Kuopio, Finland; Marja R. Sutinen, Liisantie 2 B 7, FIN-71800 Siilinjärvi, Finland; Timo P. Paronen, Kipinäkatu 32, FIN-70620 Kuopio, Finland

[21] Appl. No.: 765,766
[22] PCT Filed: Jun. 20, 1995
[86] PCT No.: PCT/FI95/00358
 § 371 Date: Jan. 7, 1997
 § 102(e) Date: Jan. 7, 1997
[87] PCT Pub. No.: WO96/01626
 PCT Pub. Date: Jan. 25, 1996

[30] Foreign Application Priority Data

Jul. 8, 1994 [GB] United Kingdom .................. 9413866

[51] Int. Cl.⁶ .................................................. A61F 13/00
[52] U.S. Cl. ........................................ 424/449; 424/489
[58] Field of Search ............................. 424/449, 489

[56] References Cited

U.S. PATENT DOCUMENTS

| | | | |
|---|---|---|---|
| 4,749,574 | 6/1988 | Ueda | 424/448 |
| 4,756,710 | 7/1988 | Bondi et al. | 424/449 |
| 5,120,546 | 6/1992 | Hansen et al. | 424/449 |
| 5,324,718 | 6/1994 | Loftsson | 514/58 |
| 5,403,840 | 4/1995 | Vikmon | 514/236.2 |
| 5,438,067 | 8/1995 | Jalonen et al. | 514/396 |

FOREIGN PATENT DOCUMENTS

| | | |
|---|---|---|
| 0 197 504 | 10/1986 | European Pat. Off. . |
| 0 463 653 | 1/1992 | European Pat. Off. . |
| 91/09592 | 7/1991 | WIPO . |
| 92/21338 | 12/1992 | WIPO . |
| 93/07858 | 4/1993 | WIPO . |

OTHER PUBLICATIONS

"Development of a Novel Transdermal System Design", Ebert C.D. et al., J. Controlled Release, vol. 6, 1987 Amsterdam, pp. 107–111, see p. 110, figures 7,9.

"Water–activated and pH–controlled release of weak bases from silicone reservoir devices", R. Sutinen et al., International Journal of Pharmaceutics, 62 (1990) 113–118.

*Primary Examiner*—D. Gabrielle Phelan
*Attorney, Agent, or Firm*—Finnegan, Henderson, Farabow, Garrett and Dunner, L.L.P.

[57] ABSTRACT

A controlled release transdermal system for the delivery of at least one therapeutic agent comprises: a reservoir comprising (a) the therapeutic agent in ionized form and (b) a pH adjusting agent which upon uptake of water is converted to a buffer solution and (c) a cyclized polysaccharide selected from a group consisting of cyclodextrin, cyclodextrin derivative and cyclodextrin polymer, the cyclized polysaccharide being capable of improving the solubility of the therapeutic agent in the buffer solution by forming an inclusion complex with the therapeutic agent; and a reservoir wall comprising a polymer being substantially impermeable to the ionized form or to the inclusion complex form of the therapeutic agent but permeable to water and to the unionized form of the therapeutic agent. The system allows the release of a therapeutic agent which may be a weak acid or base in a manner which shows less variation between patients than previous systems.

25 Claims, 1 Drawing Sheet

INDIVIDUAL CORES SURROUNDED BY POLYMER MATRIX

TRANSDERMAL DRUG DELIVERY SYSTEM

This application is a 371 of PCT/FI95/00358, field June 20, 1995.

FIELD OF INVENTION

This invention relates to transdermal drug delivery using polymeric devices. Specifically the invention relates to a transdermal system in which steady-state drug release can be modified over a wide range.

DESCRIPTION OF PRIOR ART

Transdermal delivery is a feasible alternative route of drug administration for many drugs. Typically the drug delivery devices are based on non-porous polymers that determine the rate of drug release. The systems can, for example, comprise a drug reservoir surrounded by a polymeric membrane or a polymer matrix in which a drug is dissolved or dispersed.

Typically drug release from a transdermal delivery system is controlled by the ability of the drug to partition with respect to the rate-limiting polymer and by its diffusivity in the polymer membrane or matrix. Partitioning with respect to the membrane can be modified by the partitioning coefficient of the drug between the reservoir and the rate-limiting membrane. Diffusivity in the membrane or matrix can be controlled by the chemical and physical structure of the membrane or matrix.

The conventional reservoir device technology has some drawbacks when the drug that is to be delivered transdermally is a weak base or a weak acid. Firstly, most weak acids and weak bases are more stable in the form of their crystalline salts. Due to their polarity salts can not partition into the release rate limiting nonporous polymers and thus they are not released from the device. Secondly, when free acids and bases are used in the delivery devices they partition during the storage in the release rate limiting polymers. This causes an unpredictable rise in drug concentration in the membranes and an initial high rate of drug release after application of the device. Clinically the initial release burst may be desirable or undesirable depending on the drug. The initial release burst shortens the time delay before steady drug levels are achieved in the body, but at the same time skin irritation by some drugs may be intensified.

An attempt to overcome the problems relating to the storage of drugs which are weak acids and weak bases is described in U.S. Pat. No. 4781924. This patent discloses a transdermal system where the therapeutic agent, which in the active form is either an acid or a base, during the storage of the preparation exists as a salt which is not able to migrate from the reservoir containing said therapeutical agent. The transdermal preparation further contains an activating agent, an acid or a base, which exists in an anhydrous powder form during storage. When the transdermal preparation is placed on the skin, moisture from the skin diffuses into the system and converts the activating agent to the corresponding acid or base solution which further converts the salt form of the therapeutic agent to the corresponding free acid or free base.

The system described above is an essential improvement with respect to the storage problems, but in many cases dissolution rate of the solid drug particles may become rate-limiting factor in drug release. Due to this drug release rate can not be controlled by the activating agent.

Steady-state release of weak bases/acids can be controlled by using appropriate pH-adjusting buffers. Release rate of drugs from transdermal systems can be controlled over a range of orders of magnitude by devices in which anhydrous drug salt and suitable pH-adjusting buffer mixture are dispersed or encapsulated in non-porous polymer (Sutinen et al., Int J Pharm 62: 113–118, 1990). Upon imbibition of water in the system anhydrous drug salt and buffers are dissolved. Partitioning of the drug into the polymer and its rate of release are determined by the degree of ionization of the dissolved drug, which in turn is controlled by pH. Only the unionized form of the drug partitions into the polymer. However, drug solubility may cause problems and limit the applicability of buffers to release control. Poor solubility and slow dissolution rate of the drug at the pH of the buffer may control drug release instead of the buffering mixture and the polymer. At higher pH weak bases are unionized and poorly water soluble and with weak acids opposite is true. At high pH poor water-solubility of the weak base drug may control drug release.

Cyclodextrins are cyclic oligosaccharides which are capable of forming inclusion complexes with numerous compounds. The outer surface of the cyclodextrin molecules is usually hydrophilic enabling cyclodextrins to dissolve in water, while the inner cavity of the cyclodextrins is hydrophobic in nature. The inclusion complexes are usually formed in water medium so that hydrophobic compound, e.g. a drug, is enclosed in the cavity of cyclodextrin. Since the formed inclusion complex has higher water-solubility than the drug itself, water-solubility of many compounds can be increased by cyclodextrins. Consequently, as dissolution rate of powders is related to the ultimate solubility, cyclodextrins increase also the dissolution rate of poorly soluble compounds in water.

The effect of cyclodextrins on transdermal drug delivery has been studied in hydrophilic vehicles, like gels and hydrophilic ointment bases. International patent application WO 91/09592 describes a transdermal system with a reservoir layer where the drug release rate is controlled by dissociation of an inclusion complex of cyclodextrin and the active substance. Cyclodextrin and active substance are in a gel like hydrophilic vehicle.

It is known that dissociation of cyclodextrin-drug inclusion complexes is very rapid, in the order of milliseconds. In the system of WO 91/09592 complexes dissociate as free drug is released and absorbed into the skin. Consequently, the equilibrium between the complexed and free drug as well as the release rate are controlled by drug permeation in the skin. In the invention of WO 91/09592 skin is rate-limiting and determines also the rate of drug dissociation from the cyclodextrin inclusion complex. The negative feature in this kind of system is that the skin permeability crucially affects the drug release in vivo, and, consequently, drug levels in the patients' blood may show considerable intra- and inter-individual variation, as skin permeability varies a lot.

It is thus previously known that drugs can be included in transdermal systems in the form of cyclodextrin complexes. However, such complexes have not been used nor suggested to be used for controlling the drug release from the system in accordance with the present invention.

SUMMARY OF THE INVENTION

The present invention provides a transdermal drug delivery system, or device, that permits the use of stable solid salts of weak bases and weak acids as drugs and enables to adjust the drug release rate in a wide range. The drug delivery system enables the steady-state drug release to be controlled over a wide range without changing the rate-limiting polymer. This effect is obtained by adding a cyclodextrin and an appropriate pH adjusting agent to the transdermal system. If the drug to be released is a weak base then buffer solutions of higher pH-values increase the delivery rate. If the drug is a weak acid then buffer solutions of lower pH increase the delivery rate. With cyclodextrins in the trandermal patch, it is possible to maintain the dissolution rate adequate at all pH values so that the release rate can be controlled by the pH-adjusting agent and the polymer. Changing or modifying the release rate limiting polymer offers further possibilities for modifying the release behavior.

The present invention provides a controlled release transdermal system for the delivery of at least one therapeutic agent and which comprises:

a reservoir comprising (a) the therapeutic agent in ionized form and (b) a pH adjusting agent which upon uptake of water is converted to a buffer solution and (c) a cyclized polysaccharide selected from a group consisting of cyclodextrin, cyclodextrin derivative and cyclodextrin polymer, the cyclized polysaccharide being capable of improving the solubility of the therapeutic agent in the buffer by forming an inclusion complex with the therapeutic agent; and a reservoir wall comprising a polymer being substantially impermeable to the ionized form or to the inclusion complex form of the therapeutic agent but permeable to water and to the unionized form of the therapeutic agent.

BREIF DESCRIPTION OF HTE DRAWINGS

DETAILED DESCRIPTION

Figure 1:
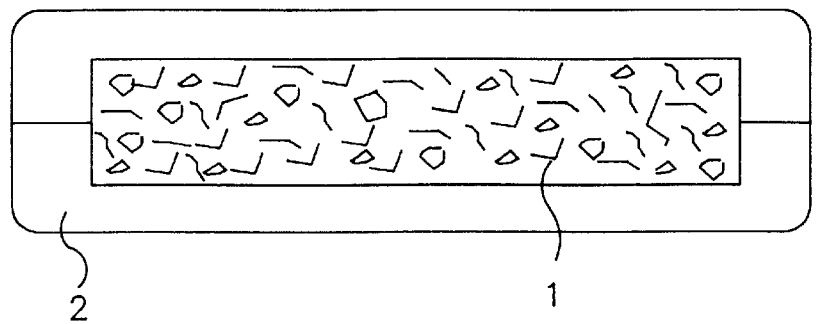
FIG. 1 is a schematic drawing of embodiments of the invention in which the drug and adjuvants are in dry state or in a vehicle in the device core.
Figure 2:
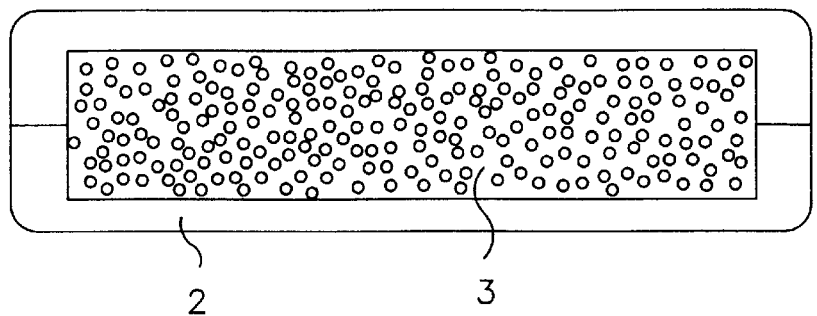
FIG. 2 is a schematic drawing of a transdermal drug delivery system showing embodiments of the invention in which the drug and adjuvants are in microcapsules or in microspheres in the device core.
Figure 3:
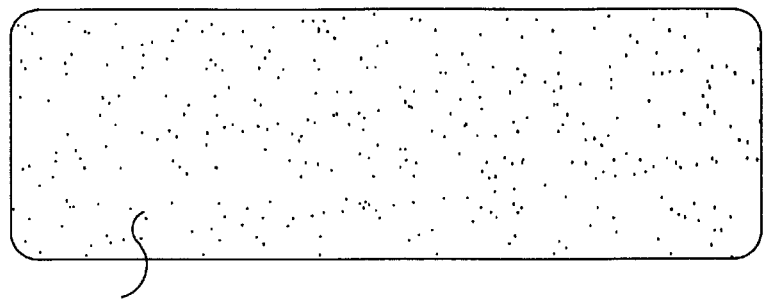
FIG. 3 is a schematic drawing of a transdermal drug delivery system showing embodiments of the invention in which the drug and adjuvants are as microspheres or coprecipitates in small individual cores of the device surrounded by rate controlling polymer matrix.

The basic components of the transdermal drug delivery system of this invention are a reservoir and a release rate-limiting reservoir wall. As depicted in FIGS. 1 and 2 the reservoir may comprise a single macroscopic core (1,3) which is surrounded by a release rate-limiting reservoir wall (2) which may be a membrane. Alternatively there may be a plurality of small individual cores which may be located in a polymer matrix that acts as a reservoir wall for each core (FIG. 3).

The core contains a drug in its solid-state salt form. In addition to the drug the core contains a cyclodextrin and a pH-adjusting agent as adjuvants. The core can also contain a vehicle in which the drug is placed that does not affect the release (e.g., Silastic adhesive or other semi-solid vehicle). The polymer matrix can optionally be surrounded by a rate-limiting polymer membrane. The system can also contain a release liner and adhesive and backing layers.

The pH-adjusting agent is in anhydrous form and is converted to a solution of the corresponding acid, neutral or alkaline buffer upon contact with water. The therapeutic agent is in the form of a solid salt and it is capable of being converted to the corresponding free acid or free base by a buffer. The release rate of the therapeutic agent from the transdermal system is regulated by controlled solubilization of the salt form of the therapeutic agent and by controlled conversion of the salt form of the therapeutic agent to its corresponding free acid or free base form.

pH-adjusting agents affect the pH of the core when water diffuses into the core after application of the device to the skin. The possible adjuvants include mono-, di-, and tribasic salts of phosphates, Tris-buffer, carbonates, bicarbonates, acetates, sulphates, sulphites, borates, citrates, nitrates, etc. When the resulting pH in the core of the system is increased by the buffer solution the fraction of non-ionized weak base drug in the core is increased and drug penetration into the non-porous polymer membrane is increased. In the case of a weak acid the decreased pH caused by the pH-adjusting buffering agent improves the permeation from the device core across the rate-limiting membrane. The pH-adjusting agent triggers and controls the rate of drug release with the diffusion of water into the core. Typically, as the fraction of unionized drug and the polymer/water partitioning of the drug are increased, at the same time, however, the water solubility of the drug is decreased, sometimes drastically. This limits the amount of available dissolved drug that could partition into the polymer, and, consequently, release rate of the drug can not be controlled by the pH-adjusting agent and polymer partitioning phenomena, but instead are solubility limited. With weak bases at high pHs in the device core and in the case of weak acids at low pHs the solubility of the poorly water-soluble unionized form of the drug can be improved by cyclodextrin inclusion complexation. Upon partitioning of the free unionized drug from the device core to the polymer membrane more drug is released correspondingly from the complexes. Thus, the release rate is controlled at all pH values by the core pH and subsequent partitioning and diffusion of the free unionized drug in the polymer membrane. This invention provides proper control of drug release rate by the device, drug is dissociated from the cyclodextrin complex at designed rate of drug release from the patch. In the present invention drug levels in the body are expected to show less variation among patients.

Cyclodextrins increase the water solubility of many drugs by complexing them into the hydrophobic cavity of cyclodextrin. In the present invention anhydrous cyclodextrin is used as a mixture with powders of the drug and pH-adjusting agents. Due to the increased solubility also the dissolution rate of the drug is increased, possibly decreasing the lag time before steady state drug release. After water imbibition higher drug concentration in the solution is achieved, but part of the dissolved drug is as complex with cyclodextrin. From the complex drug is released immediately at the same rate at which free unionized drug partitions to the polymeric membrane. The cyclodextrin-drug complex does not permeate in the nonporous polymer membrane.

Suitable cyclodextrins include without limitation natural cyclodextrins (α, β, γtype), cyclodextrin derivatives (e.g. alkylated cyclodextrins, hydroxyalkylated cyclodextrins, sulphated cyclodextrins), cyclodextrin polymers (composed of α, β and/or γcyclodextrins) and branched cyclodextrins.

This release controlling technology is applicable to salts of all weak acids and weak bases whose non-ionized form has adequate permeability through the rate-controlling polymer.

The control of the release rate of the therapeutic agent from the transdermal system of this invention is governed by the solubility and the degree of ionization of the therapeutic agent. The desired release rate can be achieved by selecting a suitable pH-adjusting agent(s) and pH in the device core, by choice of cyclodextrin type, and by the molar ratio of drug and cyclodextrin amounts precomplexed or mixed in the device.

The device can be used for controlled release of variety of drugs. In particular the device may be used for poorly water-soluble drugs and for drugs with pH-dependent solubility profiles (weak acids, weak bases). Therapeutic agents that can be delivered with this system include without limitation beta-adrenoceptor blocking agents, analgesics, anti-arrhytmic agents, antibacterial agents, anticonvulsants, antidepressants, antihistamines, antihypertensives, antipsychotics, anti-ulcer compounds, bronchodilators, diuretics, hypoglycaemic compounds, parasympathomimetics, sympathomimetics, and vasodilators. The device is useful for the administration of drugs over a sustained period of time or drugs that are difficult to administer by other means, like osmotic devices, due to their poor water solubility. This invention has also particular utility in administration of drugs with very pH dependent solubilities. For example, dexmedetomidine, a selective $\alpha_2$-receptor agonist is this kind of compound. Dexmedetomidine is a relatively lipophilic weak base (logP at pH 7.4 is 2.8) and its aqueous solubility drops dramatically as pH is increased.

In the drug delivery system a drug and adjuvants can be simply mixed as a homogenous powder mixture or coprecipitated, spray dried, microencapsulated or lyophilized together. Also, the drug and adjuvants can be dissolved and dispersed in a polymer matrix that does control the release. They can be dispersed as a powder mixture, a spray dried or lyophilized powder or as microparticles or microcapsules. Instead of blending the drug and cyclodextrin with pH-adjusting agents also precomplexed drug with cyclodextrin can be used. Drug-cyclodextrin complex can be prepared according to methods well known to a person skilled in the art. For example, spray drying, freeze drying, kneading, coprecipitation, grinding, melting or sealed heating methods can be used.

The rate-limiting reservoir wall of the device is a suitable semipermeable polymer. This means that it does not allow penetration of the ionized salts nor the cyclodextrin-drug-inclusion complex from the system core across the polymer. The polymer permits adequate penetration of water into the core. It also allows diffusion of the non-ionized base or acid from the core across the polymer, but does not allow leakage of ionized drug or the inclusion complex or adjuvants from the device. pH in the system core and the degree of ionization and solubilization of the drug determine how much drug partitions in the polymer.

Suitable materials for forming the reservoir wall include without limitation elastomer-type polymers such as silicone polymers, polyisobutylene and siliconepolyethyleneoxide copolymers, and other polymers with suitable permeabilities such as ethylene vinyl acetate copolymer, polyurethane and polyhydroxyethyl methacrylate. The reservoir wall of a single core reservoir system can be prepared by solvent casting, compression molding and by other known methods. The polymer matrix can be prepared by compression, compression molding, injection molding, solvent casting and other known methods.

Rate of water influx through the reservoir wall can be accelerated by adding hydrophilic adjuvants to the polymer (e.g. mannitol, polyethylene glycols, glycerol, sucrose, sodium chloride, potassium chloride, etc.). Also, the release rate of hydrophilic drugs can be increased by making the reservoir wall more hydrophilic.

Various materials and methods suited for the fabrication of the transdermal system according to this invention are described for example in Materials for drug delivery by M. R. Brunstedt and J. A. Anderson (in Materials Science and Technology. A Comprehensive Treatment. Cahn, R. W., Haasen, P., Kramer, E. J. (eds.) Vol 14, Medical and Dental Materials, VCH, Weinheim, 1992, p. 374–413); in Materials selection for transdermal delivery systems by R. W. Baker and J. Heller (in Transdermal Drug Delivery. Hadgraf, J., Guy, R. H. (eds.) Marcel Dekker Inc., New York, p. 293–311); in New opportunities for controlled drug delivery based on silicone polymer technology by A. Etienne (in S.T.P. Pharma 1990, Vol 6, p. 33–40); in The energy role of silicone used in transdermal drug delivery systems by X. Thomas and W. K. Pfister (in S.T.P. Pharma Sciences 1991, Vol 1, p. 38–46); in The use of biocompatible polymers in rate-controlled drug delivery systems by Y. W. Chien (in Pharmaceutical Technology 1985, Vol 9, p. 50–66); in Development concepts and practice in transdermal therapeutic systems by Y. W. Chien (in Transdermal Controlled Systemic Medications. Chien, Y. W. (ed.) Marcel Deccer Inc., New York, 1987, p. 25–81); in Pressure sensitive adhesives: science and engineering by M.C. Musolf (in Transdermal Controlled Systemic Medications. Chien, Y. W. (ed.) Marcel Deccer Inc., New York, 1987, pages 349–364); in Development of processes and technology for adhesive-type transdermal therapeutic systems (in Transdermal Controlled Systemic Medications. Chien, Y. W. (ed.) Marcel Deccer Inc., New York, 1987, pages 365–378); and in Product development and technology transfer for transdermal therapeutic systems by D. J. Bova et al. (in Transdermal Controlled Systemic Medications. Chien, Y. W. (ed.) Marcel Deccer Inc., New York, 1987, pages 379–396).

Because the drug does not penetrate through the reservoir wall in its salt form, it does not penetrate into the reservoir wall during storage. When the system is applied to the skin water must penetrate through the reservoir wall into the core, where it dissolves part of the drug and cyclodextrin and pH-adjusting agent. A non-ionized uncomplexed portion of the drug in solution starts to penetrate the reservoir wall. During these initial stages the rate of the drug release slowly increases until the drug concentration in the reservoir wall reaches steady-state levels.

Clinically the time lag before constant release lengthens the delay before steady drug levels are achieved in plasma. This can be avoided by loading the reservoir wall of a single core reservoir system with the drug before the system is manufactured to give a priming dose of the drug. The loading of the reservoir wall can cause an initial burst of faster drug release. In the case of the multiple core reservoir system the optional rate-limiting polymer membrane surrounding the matrix is loaded, or additional drug containing layer is added to the matrix. Also or only the adhesive layer can be loaded with the drug. The magnitude of the burst or delay in the drug release can be modified by varying the amount of drug that is loaded.

Skin permeation enhancers may be incorporated into the reservoir wall or into the adhesive layer to improve the skin permeability of the drug to be administered.

The aforementioned literature and patents describe a wide variety of materials and methods which can be used for fabricating the transdermal delivery systems according to this invention. This invention therefore contemplates the use of materials other than those specifically disclosed herein.

EXAMPLE 1

The effect of cyclodextrin on the solubility of dexmedetomidine

The phase-solubility diagram of dexmedetomidine (DEX) in aqueous 2hysroxypropyl-$\beta$-cyclodextrin (2-HP-$\beta$-CD) solutions (0–50% m/V or 0–349 mM) determined in three different pHs. The excess amount of the drug was added to pH 6.0, 7.0 and 8.0 phosphate buffers (142 mM) and the pHs of the suspensions were readjusted with 0.2M NaOH. The suspensions were shaken at 32° C. in a water bath for 10 days. After equilibration, the saturated solutions of DEX were filtered, diluted and the concentrations of DEX were analyzed by RP-HPLC at 210 nm.

The effect of 2-HP-β-CD on the solubility of DEX was evident (Table 1). For example, the addition of 50% (m/V) of 2-HP-β-CD to the buffer solutions improved the solubility of DEX 19–99 times. The influence of 2-HP-β-CD was the greatest as the pH of the solutions was highest, and DEX was mostly in the unionized, poorly water soluble form.

TABLE 1

Effect of 2-HP-β-cyclodextrin on the solubility of dexmedetomidine at 32° C.

| CD concentration | | DEX solubility (mg/ml) | | |
|---|---|---|---|---|
| % (m/V) | (mM) | pH 6 | pH 7 | pH 8 |
| 0 | 0 | 1.953 | 0.224 | 0.134 |
| 5 | 35 | 7.064 | 1.600 | 1.232 |
| 10 | 70 | 10.017 | 3.043 | 2.256 |
| 15 | 105 | 12.796 | 4.906 | 3.767 |
| 30 | 209 | 20.939 | 9.326 | 7.199 |
| 50 | 349 | 36.824 | 12.846 | 13.259 |

EXAMPLE 2

The effect of cyclodextrin on the release rate of dexmedetomidine from silicone depot patches The effect of cyclodextrin on the release rate of DEX was determined using reservoir-type silicone depot patches. Typical composition of the reservoir containing the drug and CD in molar ratio 1:1 was:

| DEX HCl | 200 μg | (170 μg DEX base) |
|---|---|---|
| pH-adjusting agent | 1600 μg | |
| 2-HP-β-CD | 1400 μg | | and without CD:

| DEX HCl | 2000 μg | (1700 μg DEX base) |
|---|---|---|
| pH-adjusting agent | 2000 μg | |

Tris-buffer (TRIS), trisodium phosphate (TP), disodium phosphate (DP), sodium phosphate (MP) or the mixture of disodium and sodium phosphates (50/50) (MP/DP) were used to buffer the devices. 2-HP-β-CD was added to the device in three different ways:
 1) without precomplexation with DEX
 2) using an inclusion complex of DEX and CD prepared by grinding
 3) using an inclusion complex of DEX and CD prepared by spray-drying In some patches the amount of pH-adjusting agent (DP) was decreased from 1600 μg to 200 μg or 2-HP-γ-CD was used instead of β-derivative.

Silicone membranes for the devices were made of MDX-4-4210 medical grade elastomer (Dow Corning, Midland, Miss.) by mixing 10% (w/w) MDX-4240 curing agent with the elastomer. Upon compressing at 60° C. for 1 hour the mixture is vulcanized (crosslinks) via platinum catalyst addition (hydrosilylation) reaction. DEX HCl was placed with or without pH-adjusting additives and/or cyclodextrins on a cut piece of silicone membrane. Another silicone membrane was glued on the former with Silastic™ Adhesive type B (Dow Corning, Valbonne, France) so that the drug and, if present, adjuvants were encapsulated inside two membranes. The thickness of the rate-limiting membrane in the devices was about 120 μm and the surface area of drug permeation was 0.64 cm².

In vitro release of DEX from the devices was determined in diffusion cells at 34 ±1° C. The device and a glass plate were placed in the diffusion cell so that 0.64 cm² of the device was exposed to the dissolution medium. To assess the effect of skin on drug release, a piece of epidermis was placed between the device and buffer solution. In both tests, pH 7.4 phosphate buffer (100 mM, 3 ml) was used as the receiver phase. At predetermined times, samples of 250 μl were withdrawn, replaced by fresh buffer solution, and the concentration of DEX in the samples was analyzed by RP-HPLC. After each release experiment pH in the devices was measured with a microelectrode.

DEX release from unbuffered devices with and without DEX was negligible (Table 2). The rate of DEX release from the devices was enhanced significantly by increasing the pH in the device core with pH-adjusting agents. For example, trisodium phosphate increased DEX release rate over 180 times. With increasing pH the fraction of unionized weak DEX base is increased and drug partitioning and permeation is improved. With the tested buffers rate of DEX release could be controlled over 25-fold range.

Addition of CD (without precomplexation with DEX) to the buffered devices increased DEX release rate 2.7–5.5 times. The effect of CD was increasing with increasing the pH of the device core. The largest drug release enhancement was obtained using the DEX-CD inclusion complex prepared by spray-drying (Table 2). Typically 50% of the drug dose was delivered in 48 h from this kind of devices. Neither the decrease in the amount of buffer in the device core (1600 μg ->200 μg) nor the type of cyclodextrine derivative (2-HP-γ-CD ->2-HP-γCD) did affect the rate of DEX release from the devices (Table 2).

TABLE 2

Effect of 2-HP-cyclodextrin (CD), its type (β or γ) and the amount of the buffers on the release of dexmedetomidine (DEX) from silicone depot patches at 32° C. MP = monosodium phosphate, DP = disodium phosphate, TP = trisodium phosphate and TRIS = tris-buffer (mean ± SE; n = 4–6).

| COMPOSITION | pH in the patch | Release rate (μg/h/cm²) | Release rate (% h) | Enhancement factor[a] | Release in 48 h (%) |
|---|---|---|---|---|---|
| DEX HCl | — | 0,034 ± 0,008 | 0,0013 ± 0,0003 | | 0,1 (72 h) |
| DEX + CD | — | 0,114 ± 0,065 | 0,054 ± 0,031 | 41,5× | 2,8 |
| DEX + MP | 3,6 ± 0,1 | 0,29 ± 0,05 | 0,011 ± 0,002 | | 0,5 |
| DEX + MP + CD | 4,4 ± 0,1 | 0,08 ± 0,02 | 0,030 ± 0,009 | 2,7× | 1,2 |
| DEX + MP/DP | 4,8 ± 0,1 | 7,82 ± 0,64 | 0,294 ± 0,024 | | 14,4 |
| DEX + MP/DP + CD | 6,2 ± 0,1 | 2,40 ± 0,26 | 0,898 ± 0,097 | 3,1× | 39,7 |
| DEX + DP | 5,8 ± 0,1 | 5,43 ± 0,33 | 0,204 ± 0,012 | | 10,0 |
| DEX + DP + CD | 7,7 ± 0,1 | 2,35 ± 0,26 | 0,895 ± 0,099 | 4,4× | 42,2 |

TABLE 2-continued

Effect of 2-HP-cyclodextrin (CD), its type (β or γ) and the amount of the buffers on the release of dexmedetomidine (DEX) from silicone depot patches at 32° C. MP = monosodium phosphate, DP = disodium phosphate, TP = trisodium phosphate and TRIS = tris-buffer (mean ± SE; n = 4–6).

| COMPOSITION | pH in the patch | Release rate ($\mu$g/h/cm$^2$) | Release rate (% h) | Enhancement factor[a] | Release in 48 h (%) |
|---|---|---|---|---|---|
| [DEX + CD][b] + DP | 7,6 ± 0,1 | 1,91 ± 0,15 | 0,736 ± 0,059 | 3,6× | 34,1 |
| DEX + DP + CD | 6,2 ± 0,1 | 3,13 ± 0,18 | 1,195 ± 0,07 | 5,8× | 53,1 |
| (170 $\mu$g + 200 $\mu$g + 1400 $\mu$g) | | | | | |
| (DEX + CD)[c] | 5,4 ± 0,1 | 0,05 ± 0,01 | 0,015 ± 0,003 | | 0,7 |
| (DEX + CD) + DP | 7,7 ± 0,1 | 3,17 ± 0,22 | 1,027 ± 0,07 | 5,0× | 46,4 |
| (DEX + CD) + DP | 6,5 ± 0,1 | 3,01 ± 0,17 | 0,975 ± 0,06 | 4,8× | 42,7 |
| (166 $\mu$g + 1403 $\mu$g + 200 $\mu$g) | | | | | |
| DEX + gCD + DP | 7,7 ± 0,2 | 2,50 ± 0,04 | 0,947 ± 0,01 | 4,6× | 42,5 |
| DEX + TP | 6,4 ± 0,1 | 6,44 ± 0,22 | 0,242 ± 0,008 | | 12,1 |
| DEX + TP + CD | 10,3 ± 0,2 | 2,13 ± 0,25 | 0,811 ± 0,096 | 3,4× | 38,5 |
| DEX + TRIS | 8,2 ± 0,1 | 4,27 ± 0,33 | 0,161 ± 0,013 | | 7,6 |
| DEX + TRIS + CD | 9,0 ± 0,1 | 2,44 ± 0,28 | 0,877 ± 0,100 | 5,5× | 42,4 |

[a]release rate with CD compared to that without CD
[b][ ] = DEX-CD inclusion complex prepared by grinding
[c]( ) = DEX-CD inclusion complex prepared by spray drying

What is claimed is:

1. A controlled release transdermal device for the delivery of a therapeutic agent, comprising a reservoir and a reservoir wall,
   wherein said reservoir comprises:
   (a) said therapeutic agent in the form of a solid-state salt,
   (b) a solid-state pH-adjusting agent, wherein said agent is converted to a buffer solution upon uptake of water, and
   (c) a cyclized polysaccharide selected from the group consisting of a cyclodextrin, a cyclodextrin derivative, and a cyclodextrin polymer, wherein said cyclized polysaccharide is capable of improving the solubility of said therapeutic agent in the buffer solution by forming an inclusion complex with said therapeutic agent; and
   wherein said reservoir wall comprises a polymer, wherein said polymer is substantially impermeable to the ionized form or to the inclusion complex of said therapeutic agent but is permeable to water and to the unionized form of said therapeutic agent,
   wherein the conversion of said solid-state pH-adjusting agent to the buffer solution determines the unionization of said therapeutic agent.

2. The transdermal device according to claim 1, wherein said cyclodextrin derivative is 2-hydroxypropyl-β-cyclodextrin or 2-hydroxypropyl-γ-cyclodextrin.

3. The transdermal device according to claim 1, wherein said therapeutic agent is dexmedetomidine.

4. The transdermal device according to claim 1, wherein said polymer in said reservoir wall is an elastomeric polymer.

5. The transdermal device according to claim 4, wherein said elastomeric polymer is selected from the group consisting of silicone polymers, polyisobutylene and silicone-polyethyleneoxide copolymers.

6. The transdermal device according to claim 1, wherein said reservoir is a single core containing said therapeutic agent, said cyclized polysaccharide and said solid-state pH-adjusting agent and said reservoir is surrounded by said reservoir wall.

7. The transdermal device according to claim 1, wherein said reservoir is a plurality of individual cores, each containing said therapeutic agent, said cyclized polysaccharide and said solid-state pH-adjusting agent, and each being surrounded by said polymer in said reservoir wall.

8. The transdermal device according to claim 1, wherein said device comprises a polymer matrix as said reservoir wall and contained in said matrix is a plurality of individual cores.

9. The transdermal device according to claim 1, wherein said device comprises a polymer membrane as said reservoir wall.

10. The transdermal device according to claim 1, wherein said reservoir wall is loaded with said therapeutic agent.

11. The transdermal device according to claim 1, wherein said device further comprises a rate limiting polymer membrane loaded with said therapeutic agent.

12. A process for preparing the device according to claim 1, comprising creating a reservoir of said therapeutic agent said solid-state pH-adjusting agent and said cyclized polysaccharide and placing said reservoir in contact with said reservoir wall.

13. A method of transdermal drug delivery comprising administering to a patient a controlled release transdermal device according to claim 1.

14. The transdermal device according to claim 2, wherein said therapeutic agent is dexmedetomidine.

15. The transdermal device according to claim 2, wherein said polymer in the reservoir wall is an elastomeric polymer.

16. The transdermal device according to claim 2, wherein said reservoir is a single core containing said therapeutic agent, said cyclized polysaccharide and said solid-state pH-adjusting agent and said reservoir is surrounded by said reservoir wall.

17. The transdermal device according to claim 2, wherein said reservoir is a plurality of individual cores, each containing said therapeutic agent, said cyclized polysaccharide and said solid-state pH-adjusting agent, and each being surrounded by said polymer in said reservoir wall.

18. The transdermal device according to claim 2, wherein said device comprises a polymer matrix as said reservoir wall and contained in said matrix is a plurality of individual cores.

19. The transdermal device according to claim 2, wherein said device comprises a polymer membrane as said reservoir wall.

20. Transdermal device according to claim 9, wherein said reservoir wall is loaded with said therapeutic agent.

21. The transdermal device according to claim 7, wherein said device further comprises a rate limiting polymer membrane loaded with said therapeutic agent.

22. The transdermal device according to claim 1, wherein said solid-state pH-adjusting agent is a powder.

23. A controlled release transdermal device for the delivery of a therapeutic agent, comprising a reservoir and a reservoir wall, wherein said reservoir comprises:
 (a) said therapeutic agent in the form of a solid-state salt,
 (b) a powder pH-adjusting agent, wherein said agent is converted to a buffer solution upon uptake of water, and
 (c) a cyclodextrin derivative, wherein said cyclodextrin derivative is capable of improving the solubility of said therapeutic agent in the buffer solution by forming an inclusion complex with said therapeutic agent; and wherein said reservoir wall comprises a semipermeable elastomeric polymer selected from the group consisting of silicone polymers, polyisobutylene and siliconepolyethyleneoxide copolymers, wherein the conversion of said solid-state pH-adjusting agent to the buffer solution determines the unionization of said therapeutic agent.

24. The transdermal device according to claim 23, wherein said cyclodextrin derivative is 2-hydroxypropyl-$\beta$-cyclodextrin or 2-hydroxypropyl-$\gamma$-cyclodextrin.

25. The transdermal device according to claim 23, wherein said therapeutic agent is dexmedetomidine.

* * * * *